US012064497B1

(12) United States Patent
Lueschen et al.

(10) Patent No.: US 12,064,497 B1
(45) Date of Patent: *Aug. 20, 2024

(54) AEROSOL SPRAYABLE COLOR COMPOSITION

(71) Applicant: AMERICAN SPRAYTECH, L.L.C., North Branch, NJ (US)

(72) Inventors: William Joseph Lueschen, Tampa, FL (US); Aaysha Mustafa, North Brunswick, NJ (US); Samantha F. Gribben, Carteret, NJ (US)

(73) Assignee: American Spraytech, L.L.C., North Branch, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/260,458

(22) Filed: Jan. 29, 2019

Related U.S. Application Data

(63) Continuation of application No. 15/294,933, filed on Oct. 17, 2016, now Pat. No. 11,648,188, which is a continuation of application No. 13/615,773, filed on Sep. 14, 2012, now Pat. No. 9,492,363.

(60) Provisional application No. 61/586,961, filed on Jan. 16, 2012.

(51) Int. Cl.
| | |
|---|---|
| *A61K 8/04* | (2006.01) |
| *A61K 8/19* | (2006.01) |
| *A61K 8/29* | (2006.01) |
| *A61K 8/31* | (2006.01) |
| *A61K 8/49* | (2006.01) |
| *A61K 8/58* | (2006.01) |
| *A61K 8/891* | (2006.01) |
| *A61Q 5/06* | (2006.01) |
| *B65D 83/20* | (2006.01) |
| *B65D 83/30* | (2006.01) |
| *B65D 83/32* | (2006.01) |
| *B65D 83/48* | (2006.01) |

(52) U.S. Cl.
CPC .......... *A61K 8/046* (2013.01); *A61K 8/19* (2013.01); *A61K 8/29* (2013.01); *A61K 8/31* (2013.01); *A61K 8/315* (2013.01); *A61K 8/4973* (2013.01); *A61K 8/498* (2013.01); *A61K 8/585* (2013.01); *A61K 8/891* (2013.01); *A61Q 5/06* (2013.01); *A61Q 5/065* (2013.01); *B65D 83/20* (2013.01); *B65D 83/306* (2013.01); *B65D 83/32* (2013.01); *B65D 83/48* (2013.01); *A61K 2800/43* (2013.01); *A61K 2800/87* (2013.01)

(58) Field of Classification Search
CPC ....... A61K 8/046; A61K 2800/43; A61Q 5/06
See application file for complete search history.

(56) References Cited

U.S. PATENT DOCUMENTS

| | | | |
|---|---|---|---|
| 4,209,027 A | 6/1980 | Morganroth | |
| 4,211,247 A | 7/1980 | Morganroth | |
| 5,285,916 A * | 2/1994 | Ross | B65D 83/70 220/581 |
| 6,009,881 A | 1/2000 | Baudin | |
| 6,415,800 B2 | 7/2002 | Poisson et al. | |
| 6,444,745 B1 | 9/2002 | Kilgour et al. | |
| 6,827,928 B2 | 12/2004 | Caes et al. | |
| 7,416,567 B2 * | 8/2008 | Quadir | A61K 8/8152 564/321 |
| 7,563,452 B2 | 7/2009 | Kuroda et al. | |
| 7,645,333 B2 * | 1/2010 | Serobian | C08L 83/04 106/2 |
| 2001/0007655 A1 * | 7/2001 | Paul | A61K 8/046 424/70.11 |
| 2002/0017575 A1 | 2/2002 | Andrews et al. | |
| 2003/0003064 A1 | 1/2003 | Kalla et al. | |
| 2003/0211048 A1 | 11/2003 | Halston et al. | |
| 2004/0161395 A1 | 8/2004 | Patil et al. | |
| 2004/0191197 A1 | 9/2004 | Maio et al. | |
| 2005/0142079 A1 | 6/2005 | Garrison et al. | |
| 2006/0198804 A1 | 9/2006 | Ono et al. | |
| 2006/0222615 A1 | 10/2006 | Kuroda | |
| 2007/0098646 A1 * | 5/2007 | Nappa | A61K 9/124 424/45 |
| 2007/0196291 A1 | 8/2007 | Sakuta | |
| 2009/0196841 A1 | 8/2009 | Song et al. | |
| 2009/0257966 A1 | 10/2009 | Schlossman et al. | |
| 2010/0139681 A1 * | 6/2010 | Oshika | A61Q 5/06 132/202 |
| 2011/0044925 A1 | 2/2011 | Pye et al. | |

(Continued)

FOREIGN PATENT DOCUMENTS

| | | |
|---|---|---|
| JP | 11246362 | 9/1999 |
| WO | 199408557 A1 | 4/1994 |

(Continued)

OTHER PUBLICATIONS

O'Lenick, A.J. (https://www.cosmeticsandtoiletries.com/formulating/function/pigment/118610674.html) 2011, p. 1 (Year: 2011).*

(Continued)

*Primary Examiner* — Andrew S Rosenthal (74) *Attorney, Agent, or Firm* — Renner, Kenner, Greive, Bobak, Taylor & Weber (57) ABSTRACT

An aerosol cosmetic composition is provided that includes an oil soluble gloss enhancing film forming component, a solvent, a colorant, a propellant, and useful for application to hair or skin. An aerosol dispensing system and a method of preparing an aerosol sprayable color composition are also provided.

23 Claims, 3 Drawing Sheets

(56) References Cited

U.S. PATENT DOCUMENTS

| | | | |
|---|---|---|---|
| 2012/0003167 A1* | 1/2012 | Cavazzuti | A61K 8/06 424/70.121 |
| 2012/0138078 A1 | 6/2012 | Ricard | |
| 2012/0152270 A1* | 6/2012 | Hazan | A61K 8/046 132/208 |
| 2013/0280189 A1* | 10/2013 | Thomas | A61Q 17/04 424/59 |

FOREIGN PATENT DOCUMENTS

| WO | 200021495 A1 | 4/2000 | |
|---|---|---|---|
| WO | 2006024365 | 3/2006 | |
| WO | 2010063968 A2 | 6/2010 | |
| WO | WO-2010063968 A2 * | 6/2010 | A61K 8/06 |

OTHER PUBLICATIONS

Watson, K. (www.healthline.com/health/caprylic-capric-triglyceride) pp. 1-11, Feb. 21, 2019 (Year: 2019).*
NJHealth (https://nj.gov/health/eoh/rtkweb/documents/fs/0715.pdf) Mar. 2008, pp. 1-6. (Year: 2008).*
Drugfuture.com (https://www.drugfuture.com/chemdata/polyoxyethylene-fatty-acid-esters.html). Accessed Dec. 4, 2020 (Year: 2020).*

* cited by examiner

AEROSOL SPRAYABLE COLOR COMPOSITION

CROSS-REFERENCE TO RELATED APPLICATION

This application is a continuation of U.S. application Ser. No. 15/294,933, filed on Oct. 17, 2016, and a continuation of U.S. application Ser. No. 13/615,773, filed on Sep. 14, 2012, which claims priority benefit of provisional U.S. Application No. 61/586,961 filed Jan. 16, 2012, all of which are incorporated herein by reference.

FIELD OF THE INVENTION

One or more embodiments of the present invention relate to cosmetic aerosol sprayable color compositions and dispensers thereof.

BACKGROUND OF THE INVENTION

Aerosol hair spray products containing colorant were introduced into the U.S. market in the 1970s. The aerosol color-containing hair sprays were alcohol-based aerosols composed primarily of propellant, ethyl or isopropyl alcohol, colored pigments and polyvinylpyrrolidone (PVP) monomers and their derivatives. These products typically suffered from high water solubility and rubbed off easily when touched.

To date, very little has changed in the state of the art of these products. Dimethyl silicone oils and hydrophobic surface active agents have been added in an attempt to increase water repellency but have proven to be largely ineffective. There is a need for a sprayable hair color composition that improves wearablility by providing increased adhesion, water resistance, transfer resistance, and increased gloss.

BRIEF DESCRIPTION OF THE DRAWINGS

For a full understanding of the apparatus and methods of the present disclosure reference should be made to the following detailed description and the accompanying drawings, wherein.

SUMMARY OF THE INVENTION

One or more embodiments provides an aerosol cosmetic composition comprising a solvent, a colorant, a propellant, and a gloss enhancing oil soluble film forming polymer.

Other embodiments provide an aerosol dispensing system adapted to store and dispense a composition comprising a solvent, a colorant, a propellant, and a gloss enhancing oil soluble film forming polymer.

Other embodiments provide a process for making an aerosol dispensing system comprising, combining a solvent, a colorant, and a gloss enhancing oil soluble film forming polymer with a liquefied volatile propellant in a pressurised aerosol container.

DETAILED DESCRIPTION OF ILLUSTRATIVE EMBODIMENTS

In one or more embodiments, the cosmetic aerosol color composition includes an oil soluble gloss enhancing film forming polymer, a solvent, a colorant, and a propellant. The film forming polymer, solvent and colorant may be combined to form a pre-mix prior to the addition of the propellant.

Hair gloss is sometimes also referred to as hair shine or lustre. Generally, gloss is the shiny appearance of an object placed in the path of a beam of light and is associated with specular reflection of light from the surface. As is known in the art, hair gloss can be measured subjectively, i.e. by visual inspection. Alternatively, lustre can be described by measuring the hair/light interactions using certain instruments that measure reflectances from a surface.

In one or more embodiments, the compositions of the present invention include an effective amount of a selected film forming polymer to enhance the gloss of the hair or skin to which the composition is applied. Stated another way, the compositions of the present invention provide a higher gloss on a hair or skin surface when compared to compositions that do not contain an effective amount of a gloss enhancing film forming polymer.

The gloss enhancing film forming polymer may be oil soluble. In one or more embodiments, the gloss enhancing film forming polymer advantageously binds the particulate colorants to the skin or hair.

Suitable gloss enhancing film forming polymers include low molecular weight non-polar thermoplastic polyolefins, oil soluble silicone polymers, copolymers, terpolymers, and cross polymers thereof.

Suitable non-polar thermoplastic polyolefins include polymers and copolymers prepared from monomers including paraffin (sometimes also referred to as alkane), olefin, and diolefin monomers. Suitable non-polar thermoplastic polyolefins also include hydrogenated polyolefins such as hydrogenated polycyclopentadienes, hydrogenated polyolefins. Examples of suitable monomers include piperylene, butane, butene, pentane, pentene, and cyclopentadiene.

Examples of gloss enhancing film formers include hydrogenated polycyclopentadiene, trimethylsiloxysilicate, cyclomethicone and dimethicone crosspolymers, homopolymer of isoprene, hydrogenated homopolymer of isoprene, and trimethylsiloxysilicate/dimethiconol crosspolymer.

In another embodiment, the oil soluble gloss enhancing film forming polymer may be selected from silicone resins, such as siloxysilicates. Silicone resin nomenclature is known in the art as "MDTQ" nomenclature, whereby a silicone resin is described according to the various monomeric siloxane units which make up the polymer. In one or more embodiments, the silicone resin is a MQ type of silicone resin. The letter M denotes the monofunctional unit $(CH3)_3SiO_{1/2}$. This unit is considered to be monofunctional because the silicone atom only shares one oxygen when the unit is part of a polymer. Similarly, the symbol Q denotes the tetrafunctional unit, $SiO_{4/2}$ wherein all four oxygens bonded to the silicone atom are bonded to the rest of the polymer. MQ silicone resins are sometimes referred to as siloxysilicates. A non-limiting example of a siloxysilicate is trimethylsiloxysilicate, which may be represented by the following formula: $[(CH_3)_3—Si—O]_x—(SiO_{4/2})_y$, (i.e, MQ units) wherein x and y may, for example, range from 50 to 80.

Examples of trimethylsiloxysilicate resins are designated with the INCI names trimethylsiloxysilicate (and) dimethicone, trimethylsiloxysilicate (and) cyclomethicone, trimethylsiloxysilicate (and) methyl trimethicone, and trimethylsiloxysilicate (and) ethyl trisiloxane.

In one or more embodiments, the trimethylsiloxysilicate (TMS) resin is commercially available from General Electric under the tradename SR1000 and from Wacker under the tradename TMS 803. TMS resins are also commercially available from Dow Chemical in a solvent, such as for example, cyclomethicone or dimethicone.

Silicone crosspolymers are sometimes referred to as silicone elastomers, and are based upon crosslinked dimethicone. Silicone crosspolymer gels are often provided as blends of silicone elastomer in silicone fluid, which acts as a diluent. Examples of the silicone fluid diluent include dimethicone and cyclopentasiloxane. Examples of silicone crosspolymers include cyclomethicone and dimethicone crosspolymers.

In one or more embodiments, the oil soluble film forming polymer includes ethyl trisiloxane, trimethylsiloxysilicate, and methyltrimethicone.

Gloss enhancing oil soluble film forming polymers suitable for the compositions of the present invention are commercially available from several sources. Commercially available gloss enhancing oil soluble film formers include those sold under the trade name Koboguard®, such as the Koboguard 5400 series of products, and the Koboguard MQ resins such as Koboguard MQ65TMF (available from Kobo Products), those available under the trade names RTM 2-9040 (available from Dow Corp), those available under the trade names SS4230, SS4267, SR1000 (available from Momentive), and those available under the trade names LIR-30, LIR-50, LIR200, LIR290 (available from Kurray Co.).

The gloss enhancing film forming polymer should be present in the compositions of the present invention in at least an amount that is effective to increase the gloss of the hair or skin substrate to which the composition is applied. A mixture of more than one gloss enhancing film forming polymer may be employed, so long as the total amount of gloss enhancing film forming polymer is at least an effective amount.

The effective amount of the gloss enhancing film forming polymer may be stated based upon the liquid premix, and may also be stated based upon the total aerosol spray color composition, i.e. including the propellant.

In one or more embodiments, the effective amount of film forming component is from about 3 wt. % to about 65 wt. %, in other embodiments from about 5 to about 60 wt. %, in other embodiments from about 7 to about 48 wt. %, and in other embodiments from about 10 to about 35 wt. %, based upon the total weight of the liquid premix. In certain embodiments the minimum effective amount of the gloss enhancing oil soluble film forming polymer is at least about 3 wt. %, in other embodiments at least about 7 wt. %, in other embodiments at least about 10 wt. %, in other embodiments at least about 20 wt. %, and in other embodiments at least about 35 wt. %, based upon the total weight of the liquid pre-mix.

In one or more embodiments the effective amount film forming component is from about 0.03 wt. % to about 30 wt. %, and in other embodiments from about 0.15 to about 28 wt. %, based upon the total aerosol spray color composition. In certain embodiments the minimum effective amount of the gloss enhancing oil soluble film forming polymer is at least about 0.03 wt. % of the total aerosol spray color composition, in other embodiments at least about 1 wt. % of the total composition, and in other embodiments at least about 3 wt. %, based upon the weight of the total composition.

In one or more embodiments, the compositions of the present invention may include one or more additional film forming polymers. Examples of additional oil soluble film formers include polyvinylpyrrolidone/vinyl acetate, acrylates, acrylate/silicone copolymers, polybutene, polyethylene, polyurethane-14, AMP-acrylates copolymer, acralates/octylacrylamide copolymer, polyquaternium-11, terpolymer of vinylcaprolactum/vinyl pyrrolidone and methylacrylamide.

Additional film formers are commercially available, for example, as polyvinylpyrrolidone/vinyl acetate as Luvisikol VA, by BASF Corp., polyurethane-14 and AMP-acrylates copolymer as DynamX, by Akzonobel, acralates/octylacrylamide [butylaminoethyl methacrylate?] copolymer as Amphomer LV71 by Akzonobel, polyquaternium-11 as Gafquat 755N by ISP, and terpolymer of vinylcaprolactum/vinyl pyrrolidone and methylacrylamide as Aquaflex SF-40 by ISP.

In one or more embodiments, the ratio of the gloss enhancing oil soluble film former to additional oil soluble film formers is at least about 1:4, in other embodiments, the ratio of the gloss enhancing oil soluble film former to additional oil soluble film former is at least about 1:1, in other embodiments the ratio of the gloss enhancing oil soluble film former to additional oil soluble film formers is at least about 4:1.

In one or more embodiments the aerosol spray color composition includes one or more solvents. The solvents may function as a diluent, to increase wetting, to improve spreading, to adjust particle size and/or to influence film thickness.

In one or more embodiments, the solvent is non-aqueous, and the amount of water in the composition is limited. In one or more embodiments, the amount of water in the composition is from zero to about 40 wt. %, in other embodiments, less than about 30 wt. %, in yet other embodiments, less than about 20 wt. %, in other embodiments, less than about 10 wt. %, in yet other embodiments, less than about 5 wt. %, in other embodiments, less than about 1 wt. %, based upon the total weight of the composition. In one or more embodiments, the composition is substantially devoid of water.

Suitable non-aqueous solvents include many types of organic solvents. In one or more embodiments, the non-aqueous solvent may be selected from the group consisting of silicone-containing solvents, alcohol solvents and polyol solvents, hydrocarbon solvents, esters, mineral spirits, and combinations thereof.

Examples of silicone-containing solvents include ethyl trisiloxane, methyl trimethicone, hexamethyl disiloxane, octamethylcyclotetrasiloxane, octameththyltrisiloxane, decamethyltetrasiloxane, decamethylcyclopentasiloxane, dodecamethylcyclohexasiloxane, cyclopentasiloxane, cyclohexasiloxane, hexamethyldisiloxane, polydimethylsiloxane, and polyphenylmethylsiloxane.

Examples of alcohol solvents include $C_{1-9}$ alcohols and phenoxyethanol. In one or more embodiments, the non-aqueous solvent is isopropyl alcohol, ethyl alcohol, phenoxyethanol, or a mixture thereof.

Polyols, i.e. alcohols containing multiple hydroxyl groups, include glycerine, sorbitol, butylene glycol, propylene glycol, propylene glycol, and dipropylene glycol.

Examples of hydrocarbon solvents include isododecane, squalane, squalene, isohexadecane, and isoparaffinic hydrocarbons.

The amount of the solvent may be stated based upon the liquid premix, and may also be stated based upon the total aerosol spray color composition, i.e. including the propellant.

In one or more embodiments the amount of solvent is from about 5 wt. % to about 84 wt. %, in other embodiments, from about 25 wt. % to about 72 wt. %, based upon the total weight of the liquid premix.

In one or more embodiments the amount of non-aqueous solvent in the aerosol spray color composition is from about 1.5 wt. % to about 80 wt. %, in other embodiments, from about 10 wt. % to about 60 wt. %, and in other embodiments, from about 15 wt. % to about 40 wt. %, based upon the total weight of the composition, including propellant.

In one or more embodiments, the aerosol spray color composition includes a colorant. For purposes of this specification, the term colorant is synonymous with the term coloring agent. The colorant may be considered the active ingredient or functional ingredient in the compositions of the present invention. Colorants can be used individually or as mixtures to achieve the desired colors.

Examples of colorants include FD&C aluminum lakes, FD&C calcium lakes, D&C blues, D&C browns, D&C yellows, D&C oranges, D&C reds, D&C greens, D&C ultra marines, FD&C blues, FD&C browns, FD&C yellows, FD&C oranges, FD&C reds, FD&C greens, FD&C ultra marines, black iron oxide, aluminum powder, bronze powder, chromium, chromium hydroxide, iron oxides, titanium dioxide, zinc oxide, zinc Myristate, mica, titanated mica, talc, corn starch, aluminum starch, pearlizing agents, silica, silica silyate, spherical silica, fumed silica, aluminum silicate calcium silicate, silk powder, and polyester glitter flakes. In one or more embodiments the colorant can be surface-treated with silicone, lecithin and/or amino acids.

The total amount of the colorant may be stated based upon the liquid premix, and may also be stated based upon the total aerosol spray color composition, i.e. including the propellant.

In one or more embodiments the amount of colorant is from about 0.3 wt. % to about 30 wt. %, in other embodiments, from about 0.3 wt. % to about 25 wt. %, based upon the total weight of the liquid premix.

In one or more embodiment the amount of colorant is from about 0.1 to about 20 wt. %, in other embodiments from about 0.5 to about 18 wt. %, in other embodiments, from about 0.9 to about 12 wt. %, and in other embodiments, from about 1.4 to about 8 wt %, based upon the total weight of the aerosol composition, including propellant.

Optionally, the pre-mix may include one or more additional ingredients. Optional ingredients include but are not limited to, nonionic surfactants, soaps, silicone surfactants, rheological agents, electrolytes, hair and skin conditioners, sunscreens, vitamins, botanical extracts, fragrances, and preservatives.

In one or more embodiments, the liquid pre-mix is substantially non-aqueous, i.e. the amount of water is limited, and is also substantially non-waxy. By "non-waxy" is meant that the amount of waxy components is limited. In one or more embodiments, the amount of waxy components is from zero to about 1 wt. %, based upon the total weight of the pre-mix. In other embodiments, the amount of waxy components is less than about 0.5 wt. %, in yet other embodiments, less than about 0.1 wt. %, based upon the total weight of the pre-mix.

In one or more embodiments, the compositions of the present invention are homogeneous solutions or dispersions. In other embodiments, for example when a limited amount of water is present in the composition as a diluent or to improve sprayability, the composition may be in the form of an emulsion. It will be understood by those skilled in the art that the emulsions may further comprise one or more emulsifying agents. Suitable emulsifying agents include non-ionic surfactants. Examples of non-ionic surfactants include polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl, monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-dislearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethyelen oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Generally, the pre-mix may be described as a liquid at room temperature and standard pressure. The liquid pre-mix has a viscosity that allows it to be mixed with a propellant and sprayed as an aerosol composition. The term liquid should be interpreted to include gel compositions. In one or more embodiments, the pre-mix has a viscosity under standard conditions of temperature and pressure of less than about 1000 cST, or from about 10 cST to about 1000 cST.

In one or more embodiments, all ingredients except the propellants are blended and mixed with high shear mixers to form a pre-mix batch. This pre-mix is then combined with the propellant in an aerosol dispenser adapted to store and dispense the aerosol color composition.

In one or more embodiments, the aerosol spray color composition includes a propellant. Propellants can be used individually or blended together. Advantageously, the selection of a propellant or blend of propellants may be used to achieve a particular spray pattern, control particle size, conform to government regulations, or for cost considerations.

Propellants may be selected from the group consisting of hydrocarbons, hydrofluorocarbons, ethers, and combinations thereof. Examples of hydrocarbon propellants include pentane, n-butane, isobutane, and propane. Examples of hydrofluorocarbon propellants include 1,1,1,2-tetrafluoroethane (134a) and 1,1-difluoroethane (152a). An example of an ether propellant includes dimethyl ether.

In one or more embodiments the amount of propellant is from about 20 to about 97 wt. %, in other embodiments from about 30 to about 97 wt. %, in other embodiments, from about 35 to about 96 wt. %, and in other embodiments, from about 40 to about 95 wt. %, based upon the total weight of the aerosol color composition.

Advantageously, the color compositions of the present invention may be dispensed as an aerosol spray. Therefore, the present invention provides an aerosol dispensing system. The aerosol dispensing system is not unduly limited, and may generally be described as having a container that includes an outlet and is capable of being pressurized, a valve system, and an actuator.

Figure 1:
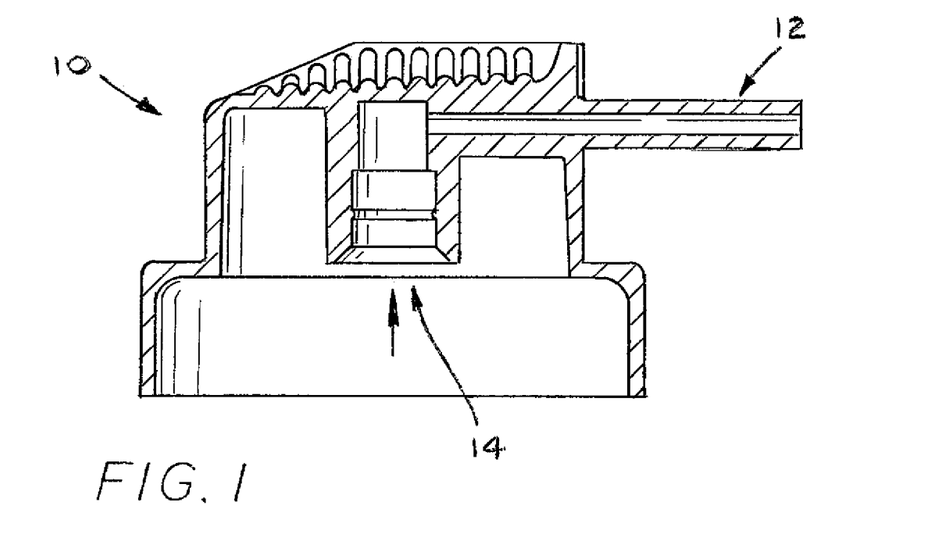
FIG. 1 is a side sectional view of an embodiment of the actuator.

Referring now to FIG. 1, an actuator is shown and generally indicated by the numeral 10. Actuator 10 includes an actuator orifice 12 and an actuator socket 14.

Figure 2:
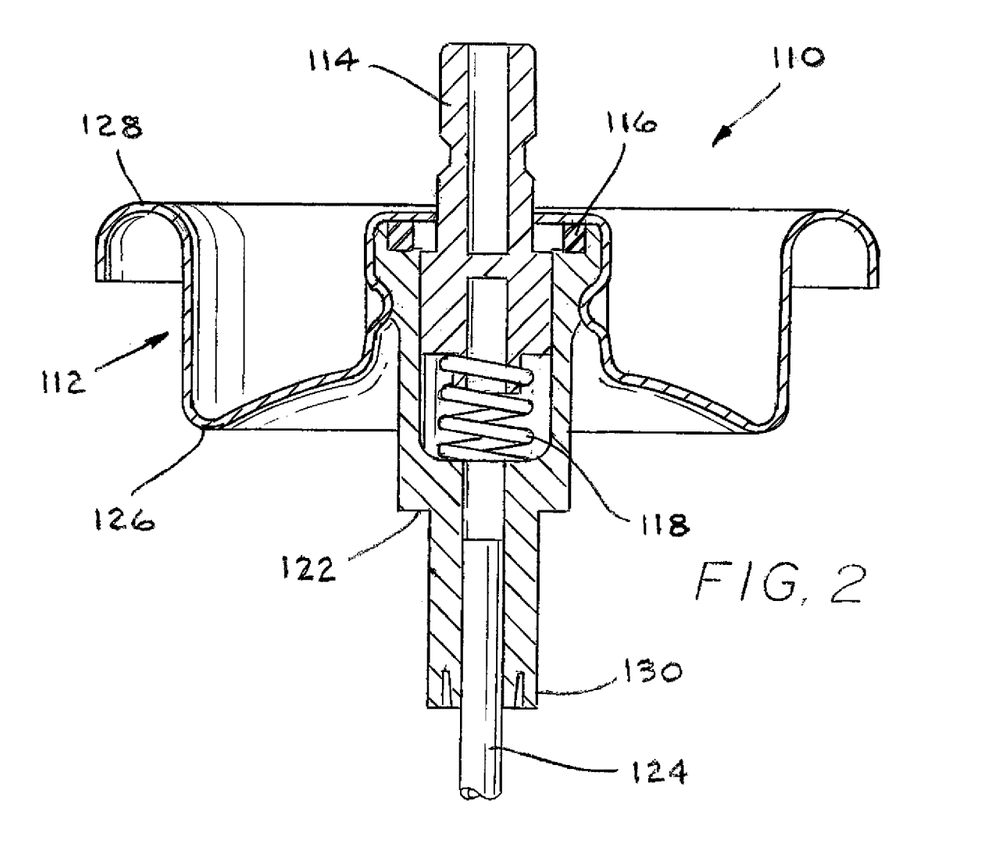
FIG. 2 is a side sectional view of an embodiment of the valve system.
Figure 3:
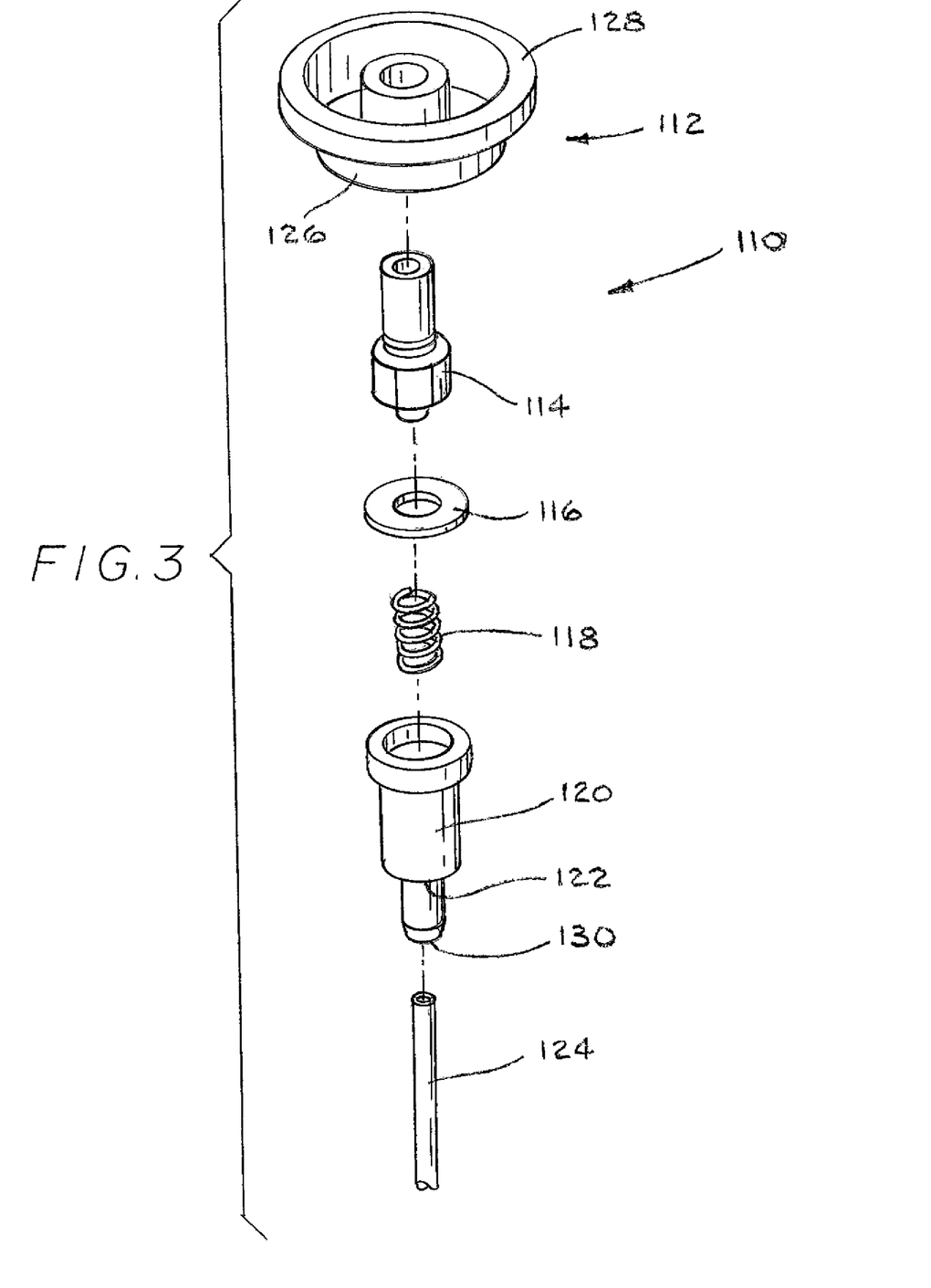
FIG. 3 is an exploded diagram of an embodiment of the valve system.

Referring now to FIGS. 2 and 3, a valve system is shown and generally indicated by the numeral 110. Valve system 110 includes a valve housing 122. For purposes of this specification, valve housing 122 may also be referred to as valve body 122. The valve housing is surrounded by a valve cup 112. The valve cup 112 includes a mounting cup 126. Under the lip of the valve cup 112 is the mounting cup gasket 128. The valve body 122 includes an entry orifice 130 which can be used to attach the dip tube 124. The valve body 122 may optionally include a vapor tap orifice 120. Between the valve body 122 and the valve cup 112 is a stem gasket 116. Within the valve body is the spring 118. Above the valve body 112 is the stem 114.

Figure 4:
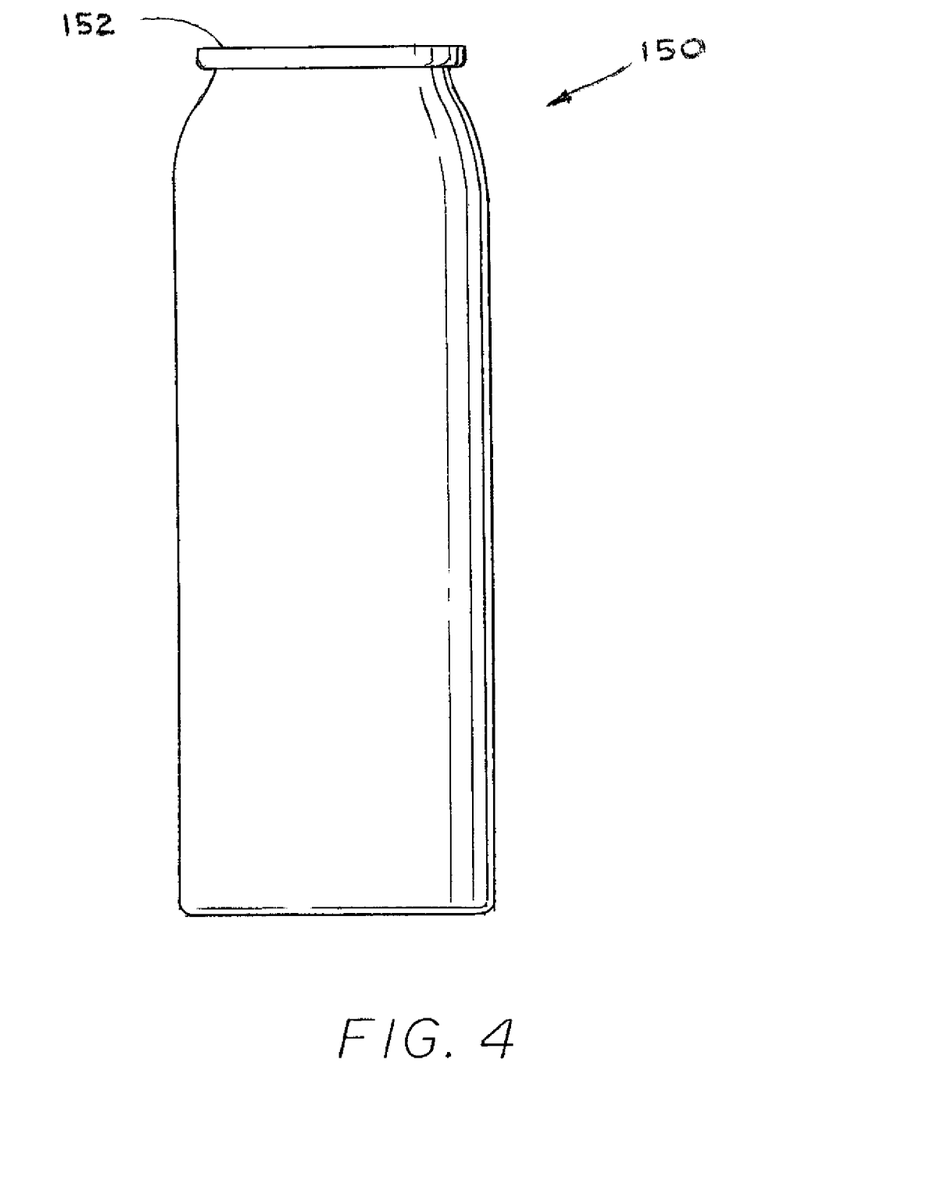
FIG. 4 is a side view of an embodiment of the can.

Referring now to FIG. 4, a can or aerosol container is shown generally indicated by the numeral 150. The can 150 includes a ridge 152.

An aerosol can 150 can be attached, for example, to a valve system 110 by placing the mounting cup gasket 126 on the ridge 152 and crimping the valve cup 112. The actuator 10 can be attached, for example, to the valve system 110 by inserting the stem 114 into the actuator socket 14.

In one or more embodiments, the present invention provides a method of manufacture of an aerosol hair colorant, the method including the steps of combining a solvent, a colorant, a gloss enhancing oil soluble film forming polymer, and optionally one or more additional ingredients, to form a liquid premix; placing said premix into an aerosol container 150; and then one of the following steps of: crimping said aerosol container and then filling said container with propellant; or filling said container with propellant and then crimping said aerosol container.

In one or more embodiments, the propellant is pressure filled through the valve system 110.

In another embodiment, the propellant is pressurized in the crimping operation. This is sometimes referred to as under the cup gassing.

In one or more embodiments, the dispenser includes a container adapted to store the aerosol color composition and having an outlet adapted to dispense the aerosol color composition. The dispenser may include a valve system and actuator connected to the outlet of the container.

The valve system 110 includes a valve stem 112, a stem gasket 116, a valve body 122, a dip tube 124, a valve cup 112, a cup gasket 128, and an entry orifice 130. The valve body may include a vapor tap orifice 120. Generally, a vapor tap orifice 120 is an opening in the valve body that allows propellant for enter the valve body 122 and mix with the liquid pre-mix, which may enter the valve body 122 via the dip tube 124. The mixing of the propellant and the liquid pre-mix in the valve body 122 in this fashion produces physical agitation that may result in a smaller mean particle size of the aerosol, and/or a faster evaporation rate of the solvent in the pre-mix. The net result is a dryer spray.

Typically, an entry orifice 130 is an opening molded into the valve body 122 at the location where the dip tube enters the valve body 122. The entry orifice may be adapted to allow control of the amount of liquid pre-mix entering the valve body 122. Restricting the amount of liquid phase that enters the valve body 122 may result in more rapid expansion of the propellant within the valve body 122. This in turn may results in a smaller mean particle size of the aerosol and/or a faster evaporation rate of the solvent in the pre-mix, again resulting in a dryer spray.

Advantageously, aerosol valves may be chosen to select the spray pattern and spray rate of a product. In combination with the propellant and solvent, the spray pattern can be altered from narrow to wide, the spray rate can be adjusted, and the wetness or dryness of the application can be increased or decreased. As described above, one method of adjusting the dryness of the spray is by employing and adjusting the vapor tap orifice 120, the valve body entry orifice 130 and the propellant level. In certain embodiments, when the level of propellant is high relative to the liquid pre-mix, the size of the vapor tap may have less effect on the wetness or dryness of the aerosol application.

In one or more embodiments, valves used in the valve system may include a sealing ring on a stem seat. Valve systems not having a sealing ring on the stem seat may experience malfunctions when employed with aerosol composition that contain particulates. The types of malfunctions that can occur include slow shut off, leakage during storage, and total blockage of the valve system.

Valves systems having a sealing ring in the stem seat largely avoid these malfunctions. In one or more embodiments, the ring presses into the sealing gasket and wipes the particulate matter from the sealing area during shut off. In one or more embodiments, the valve system includes a straight shank stem that wipes the sealing surface clean on shut off. In one or more embodiments, the stem has a high orifice, which positions the stem orifice above the sealing gasket when at rest.

Advantageously, the width or diameter of the spray pattern of the spray color composition may be adjusted. In one or more embodiments, the width of the spray pattern may be adjusted from about 8 inches to about 2 inches when sprayed from about 6 inches from the surface. In particular embodiments, the spray pattern of the spray color composition is about 8 inches wide when sprayed from about 6 inches from the surface, in other embodiments the spray pattern is about 6 inches when sprayed from about 6 inches from the surface, in other embodiments the spray pattern is about 4 inches when sprayed from about 6 inches from the surface, in other embodiments the spray pattern is about 2 inches wide when sprayed from about 6 inches from the surface. A pattern width of about 6 inches may be desirable for a product that is employed to color a large section of hair, while a pattern of about 2 inches would be desirable for a product that is employed as a root or baldness concealer.

In one or more embodiments, the spray pattern can be narrowed by increasing the length of the actuator orifice 12. In one or more embodiments, where a narrow pattern is desired, suitable actuators include barrel-type actuators with orifice lengths of about 0.25 inches or longer.

Although there are many types of valve systems and actuators that are suitable to dispense the aerosol color compositions of the present invention, exemplary valve systems for producing a narrow patterned spray include those available from Summit Valve Corporation or Precision Valve Co., with a Kosmos MiniJet actuator that is available from Precision Valve Corp. An exemplary valve for producing a wide spray is produced by Precision Valve Corp. or Lindal Valve Co. and uses a standard Kosmos type actuator.

In order to demonstrate the practice of the present invention, the following examples have been prepared and tested. The examples should not, however, be viewed as limiting the scope of the invention. The claims will serve to define the invention.

EXAMPLES

Example 1

The following ingredients, with the exception of the butane propellant, were mixed in a high shear mixer until homogeneous. The amounts of each ingredient are indicated in weight percent, based upon the total weight of the composition including the propellant. The formulation of Example 1 is useful as a Temporary Hair Coloring.

| | |
|---|---|
| ethyl trisiloxane | 3.316% |
| trimethylsiloxysilicate | 0.279% |
| methyltrimethicone | 0.150% |
| fragrance | 0.005% |
| red iron oxide | 0.157% |
| yellow iron oxide | 1.000% |
| titanium dioxide | 0.094% |
| 1,1, difluoroethane | 47.500% |
| n-butane | 47.500% |

Example 2

The following ingredients, with the exception of the butane propellant, were mixed in a high shear mixer until homogeneous. The amounts of each ingredient are indicated in weight percent, based upon the total weight of the composition including the propellant. The formulation of Example 2 is useful as an Emulsion Hair Spray.

| | |
|---|---|
| isobutane | 50.00% |
| ethyl trisiloxane | 20.15% |
| trimethylsiloxysilicate | 4.94% |
| methyltrimethicone | 2.66% |
| sorbitan Isostearate | 0.75% |
| tocopherol acetate | 0.05% |
| palmate Extract | 0.05% |
| silk powder | 0.05% |
| red Iron Oxide | 0.45% |
| Black iron oxide | 0.25% |
| yellow iron oxide | 1.80% |
| titanium dioxide | 2.02% |
| water | 15.00% |
| xanthan gum | 0.05% |
| sodium chloride | 0.50% |
| panthenol | 0.05% |
| butylene glycol | 0.50% |
| dipropylene glycol | 0.05% |
| phenoxyethanol | 0.37% |
| HD/trimethylol hexyllactone crosspolymer and silica | 0.01% |
| Mica & trithoxycaprylylsilane | 0.25% |
| fragrance | 0.05% |

Various modifications and alterations that do not depart from the scope and spirit of this invention will become apparent to those skilled in the art. This invention is not to be duly limited to the illustrative embodiments set forth herein.

What is claimed is:

1. An aerosol hair color composition consisting of:
one or more gloss-enhancing film forming polymers,
an alcohol solvent,
one or more colorants,
from about 0.1 to about 20 wt. % of aluminum starch, based upon the total weight of the aerosol composition,
an emulsifier selected from the group consisting of polyoxyethylene fatty acid esters,
optionally, one or more additional ingredients selected from the group consisting of rheological agents, electrolytes, conditioning agents, fragrances, botanical extracts, vitamins, preservatives, electrolytes, and emulsifying agents, and
one or more propellants selected from the group consisting of hydrofluorocarbons, hydrocarbons, and dimethyl ether, wherein the composition comprises less than 1 wt. % water, based upon the total weight of the aerosol hair color composition.

2. The aerosol composition of claim 1, where the composition includes about 95 wt. % of the propellant, based upon the total weight of the aerosol hair color composition.

3. The aerosol composition of claim 1, where the amount of film forming polymer is from about 3 to about 65 wt. %, based upon the total weight of the composition, not including the propellant.

4. The aerosol composition of claim 1, where the solvent is selected from the group consisting of isopropyl alcohol, ethyl alcohol, phenoxyethanol, and combinations thereof.

5. The aerosol composition of claim 1, where the amount of solvent is from about 5 to about 84 wt. %, based upon the total weight of the composition, not including the propellant.

6. The aerosol composition of claim 1, where the one or more colorant is selected from the group consisting of FD&C aluminum lakes, FD&C calcium lakes, D&C blues, D&C browns, D&C yellows, D&C oranges, D&C reds, D&C greens, D&C ultra marines, FD&C blues, FD&C browns, FD&C yellows, FD&C oranges, FD&C reds, FD&C greens, FD&C ultra marines, black iron oxide, aluminum powder, bronze powder, chromium, chromium hydroxide, iron oxides, titanium dioxide, zinc oxide, zinc Myristate, mica, titanated mica, talc, corn starch, aluminum starch, pearlizing agents, silica, silica silicate, spherical silica, fumed silica, aluminum silicate calcium silicate, silk powder, polyester glitter flakes, and combinations and surface-treated variations thereof.

7. An aerosol hair color composition comprising:
one or more gloss-enhancing film forming polymers,
an alcohol solvent,
one or more colorants,
from about 0.1 to about 20 wt. % of aluminum starch, based upon the total weight of the aerosol composition,
an emulsifier selected from the group consisting of polyoxyethylene fatty acid esters,
optionally, one or more additional ingredients selected from the group consisting of rheological agents, electrolytes, conditioning agents, fragrances, botanical extracts, vitamins, preservatives, electrolytes, and emulsifying agents, and
about 95 wt. % of one or more propellants selected from the group consisting of hydrofluorocarbons, hydrocarbons, and dimethyl ether, based upon the total weight of the aerosol hair color composition, wherein the composition comprises less than 1 wt. % water, based upon the total weight of the aerosol hair color composition.

8. The aerosol hair color composition of claim 7, wherein the amount of alcohol solvent is from about 5 to about 84 wt. %, based upon the composition not including the propellant.

9. An aerosol hair color composition consisting of:
one or more gloss-enhancing film forming polymers selected from the group consisting of polyvinylpyrrolidone/vinyl acetate, polybutene, polyethylene, polyurethane-14, AMP-acrylates copolymer, acrylates/octylacrylamide copolymer, polyquaternium-11, terpolymer of vinylcaprolactum/vinyl pyrrolidone and methylacrylamide,
ethyl alcohol,
one or more colorants,
from about 0.1 to about 20 wt. % of aluminum starch, based upon the total weight of the aerosol composition,
one or more emulsifier selected from the group consisting of polyoxyethylene fatty acid esters, polyoxyethylene fatty acid ethers, and combinations thereof,
optionally, one or more additional ingredients selected from the group consisting of rheological agents, electrolytes, conditioning agents, fragrances, botanical extracts, vitamins, preservatives, and electrolytes, and
one or more propellants selected from the group consisting of hydrofluorocarbons, hydrocarbons, and dimethyl ether, wherein the composition comprises less than 1 wt. % water, based upon the total weight of the aerosol hair color composition.

10. The aerosol composition of claim 1, where the film forming polymer is present in an amount of from 0.03 to 3 wt. %, based upon the total weight of the aerosol composition.

11. The aerosol composition of claim 9, where the film forming polymer is present in an amount of from 0.03 to 3 wt. %, based upon the total weight of the aerosol composition.

12. The aerosol composition of claim 1, where the amount of solvent is from 1.5 to 40 wt. %, based upon the total weight of the composition.

13. The aerosol composition of claim 9, where the amount of ethyl alcohol is from 1.5 to 40 wt. %, based upon the total weight of the composition.

14. The aerosol composition of claim 1, where the colorant is present in an amount of from 0.1 to 1.4 wt. %, based upon the total weight of the composition.

15. The aerosol composition of claim 9, where the colorant is present in an amount of from 0.1 to 1.4 wt. %, based upon the total weight of the composition.

16. The aerosol composition of claim 1, where the film forming polymer is selected from the group consisting of polyvinylpyrrolidone/vinyl acetate, polybutene, polyethylene, polyurethane-14, AMP-acrylates copolymer, acrylates/octylacrylamide copolymer, polyquaternium-11, terpolymer of vinylcaprolactum/vinyl pyrrolidone and methylacrylamide.

17. The aerosol composition of claim 7, where the film forming polymer is selected from the group consisting of polyvinylpyrrolidone/vinyl acetate, polybutene, polyethylene, polyurethane-14, AMP-acrylates copolymer, acrylates/octylacrylamide copolymer, polyquaternium-11, terpolymer of vinylcaprolactum/vinyl pyrrolidone and methylacrylamide.

18. An aerosol hair color composition comprising:
one or more gloss-enhancing film forming polymers;
polydimethylsiloxane;
ethyl alcohol;
one or more colorants;
one or more emulsifiers selected from the group consisting of ethoxylated castor oil, polyoxyethylene tridecyl ether, polyoxyethylene cetyl ether, glyceryl monostearate, polyoxyethylene stearyl ester, polyoxyethylene stearyl ether, polyoxyethylene tridecyl ether, polyoxyethylene cetyl ether, and combinations thereof;
one or more additional ingredients selected from the group consisting of rheological agents, electrolytes, conditioning agents, fragrances, botanical extracts, vitamins, preservatives, and electrolytes; and
one or more propellants selected from the group consisting of hydrofluorocarbons, hydrocarbons, and dimethyl ether.

19. The aerosol composition of claim 18, where the composition includes about 95 wt. % of the propellant, based upon the total weight of the aerosol hair color composition.

20. The aerosol composition of claim 18, where the amount of film forming polymer is from about 3 to about 65 wt. %, based upon the total weight of the composition, not including the propellant.

21. The aerosol composition of claim 18, further comprising an alcohol selected from the group consisting of isopropyl alcohol, phenoxyethanol, and combinations thereof.

22. The aerosol composition of claim 18, where the amount of ethyl alcohol is from about 5 to about 84 wt. %, based upon the total weight of the composition, not including the propellant.

23. The aerosol composition of claim 18, where the one or more colorant is selected from the group consisting of FD&C aluminum lakes, FD&C calcium lakes, D&C blues, D&C browns, D&C yellows, D&C oranges, D&C reds, D&C greens, D&C ultra marines, FD&C blues, FD&C browns, FD&C yellows, FD&C oranges, FD&C reds, FD&C greens, FD&C ultra marines, black iron oxide, aluminum powder, bronze powder, chromium, chromium hydroxide, iron oxides, titanium dioxide, zinc oxide, zinc Myristate, mica, titanated mica, talc, corn starch, aluminum starch, pearlizing agents, silica, silica silicate, spherical silica, fumed silica, aluminum silicate calcium silicate, silk powder, polyester glitter flakes, and combinations and surface-treated variations thereof.

* * * * *